(12) United States Patent
Balestra

(10) Patent No.: US 7,945,606 B2
(45) Date of Patent: May 17, 2011

(54) METHOD AND APPARATUS FOR EVALUATING A TIME VARYING SIGNAL

(75) Inventor: Chester L. Balestra, Wildwood, MO (US)

(73) Assignee: The Boeing Company, Chicago, IL (US)

(*) Notice: Subject to any disclaimer, the term of this patent is extended or adjusted under 35 U.S.C. 154(b) by 1075 days.

(21) Appl. No.: 11/697,661

(22) Filed: Apr. 6, 2007

(65) Prior Publication Data

US 2008/0247448 A1 Oct. 9, 2008

(51) Int. Cl.
*G06F 15/00* (2006.01)
*H03F 1/26* (2006.01)
(52) U.S. Cl. .................. 708/200; 708/207; 702/193
(58) Field of Classification Search ............. 708/207, 708/200; 702/183, 193
See application file for complete search history.

(56) References Cited

U.S. PATENT DOCUMENTS

| | | | |
|---|---|---|---|
| 4,336,595 A | | 6/1982 | Adams et al. |
| 5,754,122 A * | | 5/1998 | Li et al. .................. 340/870.11 |
| 5,847,668 A * | | 12/1998 | Morita et al. .................. 341/132 |
| 6,449,565 B1 | | 9/2002 | Budrow et al. |
| 6,618,654 B1 | | 9/2003 | Zaat |
| 7,454,297 B2 * | | 11/2008 | Balestra .................... 702/42 |
| 7,719,416 B2 * | | 5/2010 | Arms et al. ............... 340/539.1 |

OTHER PUBLICATIONS

Lopez, G. et al; "Evaluation of the Fatigue Resistance of Welded Structures for Naval Use"; Welding International, Woodhead Publishing Co.; vol. 17, No. 6; Jun. 1, 2003; pp. 451-465.
Metal Fatigue in Engineering; by Ralph I. Stephens, Ali Fatemi, Robert R. Stephens and Henry O. Fuchs, John Wiley & Sons, New York; 2001, pp. 281-286.
Downing & Socie; "Simple Rainflow Counting Algorithms"; International Journal of Fatigue, Jan. 1982; Butterworth & Co., Publishers.

* cited by examiner

*Primary Examiner* — Chuong D Ngo
(74) *Attorney, Agent, or Firm* — Law Office of Donald D. Mondul

(57) ABSTRACT

A method for evaluating a received signal varying over an interval includes: (a) obtaining a data sample and a sample time; (b) determining whether the sample exceeds a previous exceeded extremum of the signal; (c) if the sample does not exceed an exceeded extremum, storing the sample; (d) if the sample exceeds the an exceeded extremum, in no particular order: (1) extracting and storing cycle information involving the exceeded extremum; and (2) replacing an earliest exceeded extremum with the sample; (e) outputting first selected data from a storage unit; (f) determining whether the interval has completed; (g) if the interval has not completed, repeating steps (a) through (f); (h) if the interval has completed, checking whether an output buffer is empty; (i) if the buffer is not empty, outputting second selected data from the buffer; j) if the buffer is empty, terminating the method.

12 Claims, 6 Drawing Sheets

Output₁(t_k) = y₁ = Cycle range
Output₂(t_k) = y₂ = Cycle type
Output₃(t_k) = y₃ = Cycle duration
Output₄(t_k) = y₄ = Cycle mean value

METHOD AND APPARATUS FOR EVALUATING A TIME VARYING SIGNAL

TECHNICAL FIELD

The disclosure may be directed to a method and apparatus that sorts out, in substantially real time, a time-stream of randomly cyclic and variable amplitude data into a corresponding stream of magnitudes of cycles of substantially matched minimum and maximum amplitudes.

BACKGROUND

A capability to process a stream of randomly cyclic and variable data on the fly, substantially in real time, may permit one to timely determine relative maximum and minima. Such a substantially real time processing capability may also permit one to determine, sort out, and match the hierarchy of extrema (i.e., maxima or minima), greatest positive and negative excursions of the data; to determine the magnitude of each excursion set of substantially matched positive extrema and negative extrema; to determine the duration of each excursion set; and to determine mean amplitude value for each excursion set.

A determining, sorting out and matching hierarchy of signal or data excursions may be effected using the Matsuishi-Endo Rainflow Counting Method. The Rainflow Counting Method is believed to have been first published in Japanese in 1968. A good English-language description of the Rainflow Counting Method may be found in *Metal Fatigue in Engineering*; by Ralph I. Stephens, Ali Fatemi, Robert R. Stephens and Henry O. Fuchs, John Wiley & Sons, New York; 2001, pp. 281-286. The Rainflow Counting Method has been implemented in various ways to effect counting cyclic signals representing data and sorting out a history of "peaks and valleys" occurring in a stream of data. However, all implementations to date involving the Rainflow Counting Method are believed to have involved after-the-fact implementations of the method using data relating to a completed test or other generation of data. No implementation is known to have been effected for carrying out a substantially real time, on the fly, evaluation of a time varying signal, including a substantially real time sorting of peaks and valleys in a time varying signal.

There is a need for a method and apparatus for effecting substantially real time evaluation of a time varying signal that permits selection and extraction of relative maxima and minima (i.e., extrema) from the signal.

There is a need for a method and apparatus for effecting substantially real time evaluation of a time varying signal that permits substantially real time presentation of pertinent characteristics of the signal such as, by way of example and not by way of limitation, signal magnitudes, signal cycle durations and mean signal amplitudes.

SUMMARY

A method for evaluating a received signal varying over an interval includes: (a) obtaining a data sample and a sample time; (b) determining whether the sample exceeds a previous exceeded extremum of the signal; (c) if the sample does not exceed an exceeded extremum, storing the sample; (d) if the sample exceeds an exceeded extremum, in no particular order: (1) extracting and storing cycle information involving the exceeded extremum; and (2) replacing an earliest exceeded extremum with the sample; (e) outputting first selected data from a storage unit; (f) determining whether the interval has completed; (g) if the interval has not completed, repeating steps (a) through (f); (h) if the interval has completed, checking whether an output buffer is empty; (i) if the buffer is not empty, outputting second selected data from the buffer; (j) if the buffer is empty, terminating the method.

An apparatus for evaluating a received signal representing values of a parameter varying over a test interval includes: (a) a signal sampling unit coupled for sampling the received signal; the signal sampling unit obtaining an extant data sample of the signal at an extant sample time;(b) a comparing unit coupled with the sampling unit and coupled with a storage unit; the comparing unit determining whether the extant data sample exceeds at least one previous exceeded extremum of the signal stored in the storage unit; (c) a responsive unit coupled with the comparing unit; if the comparing indicates the extant data sample does not exceed the at least one previous exceeded extremum, the responsive unit effects storing of the extant data sample in the storage unit; if the extant data sample exceeds the at least one previous exceeded extremum, the responsive unit, in no particular order, effects a first response extracting and storing cycle information involving the at least one previous exceeded extremum in the storage unit; and effects a second response replacing an earliest exceeded extremum of the at least one previous exceeded extremum in the storage unit with the extant data sample; (d) an output unit coupled with the storage unit; the output unit effecting outputting first selected data from the storage unit at least one time during the test interval; and (e) a signal monitoring unit coupled with the signal sampling unit and with the storage unit; the signal monitoring unit determining when the test interval has completed; the signal monitoring unit and the signal sampling unit cooperating to obtain a next extant data sample of the signal at a next extant sample time when the test interval is not complete; the apparatus effecting treatment of the next extant data sample substantially as the treatment of the first extant data was effected; when the test interval is completed and the storage unit is not empty, the signal monitoring unit and the signal sampling unit cooperate to cease sampling the signal and present second selected data from the storage unit; when the test interval is completed and the storage unit is empty, the signal monitoring unit and the signal sampling unit cooperate to cease sampling the signal.

It may be, therefore, a feature of the embodiment to provide a method and apparatus for effecting substantially real time evaluation of a time varying signal that permits selection and extraction of relative maxima and minima (i.e., extrema) from the signal.

It may be a further feature of the embodiment to provide a method and apparatus for effecting substantially real time evaluation of a time varying signal that permits substantially real time presentation of pertinent characteristics of the signal such as, by way of example and not by way of limitation, signal magnitudes, signal cycle durations and mean signal amplitudes.

Further features of the present invention may be apparent from the following specification and claims when considered in connection with the accompanying drawings, in which like elements are labeled using like reference numerals in the various figures, illustrating the preferred embodiments of the invention.

DETAILED DESCRIPTION

The exemplary disclosed method and apparatus are capable of substantially real time tracking and rainflow processing of a time-varying signal, such as a signal representing stream-in-time data. By way of example and not by way of limitation, such substantially real time evaluation may permit substantially real time processing and tracking of mechanical fatigue as it occurs. Such substantially real time evaluation permits analyzing and correlating data in a temporal flow as the data flows, as opposed to analyzing and correlating data after-the-fact. The exemplary disclosed method and apparatus may be capable of employing rainflow processing for tracking magnitude, duration, and mean value of each data excursion cycle in substantially real time.

The Matsuishi-Endo Rainflow Method works with relative extrema of a signal, such as maxima and minima. Traditional rainflow processing deals with completed data sets collected during a now-completed data taking so that relative extrema of the signal may be known for applying the Matsuishi-Endo Rainflow Method. The Matsuishi-Endo Rainflow Method rearranges the history of the maxima and minima of the signal to start with either the "highest peak or the lowest valley". Such an arranging of data to convenience an evaluation method may not be practical for application in substantially real time analysis. It is for the purpose of accommodating substantially real time signal analysis of a time-varying signal that rainflow analysis may be uniquely adapted in the disclosed method and apparatus.

Figure 1:
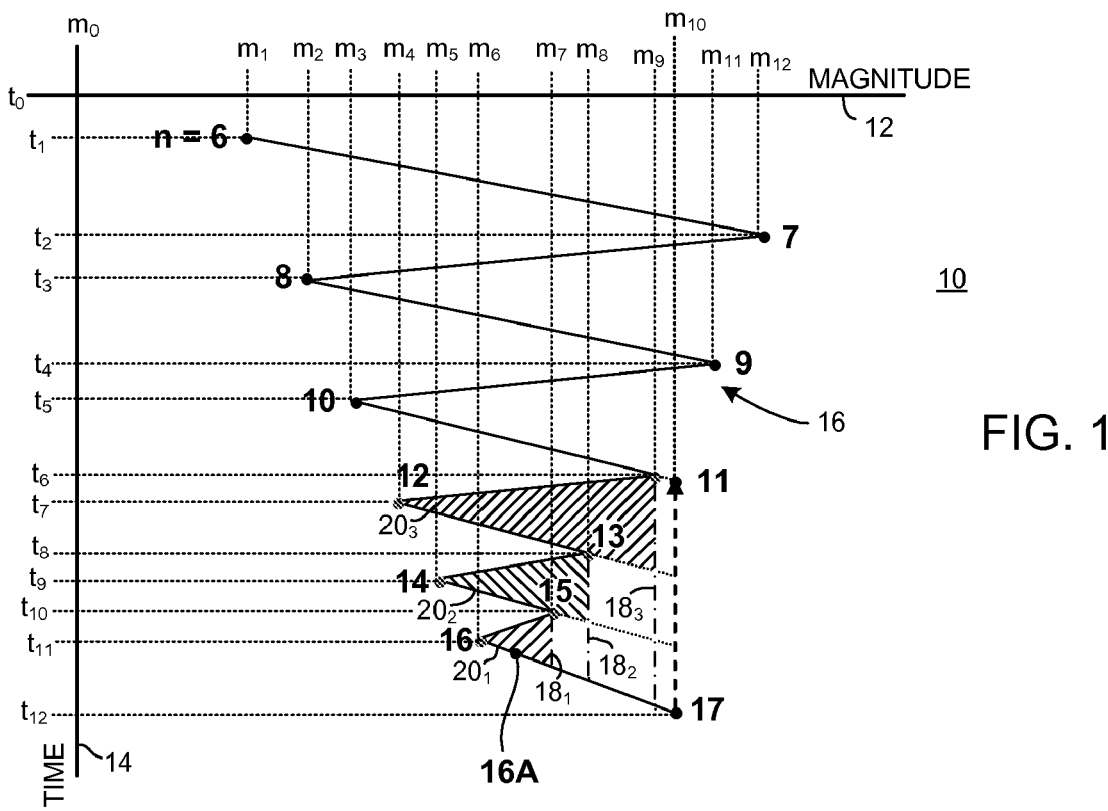
FIG. 1 is a graphic representation of evaluation of a maximum peak of a time varying signal vis-à-vis earlier-occurring maximum peaks of the signal.

FIG. 1 is a graphic representation of evaluation of a maximum peak of a time varying signal vis-à-vis earlier-occurring maximum peaks of the signal. In FIG. 1, a graphic plot 10 presents a horizontal axis 12 that may represent signal amplitude and a vertical axis 14 that may represent time. A curve 16 plotted against axes 12, 14 may represent a time-varying signal such as, by way of example and not by way of limitation, stress on a test member as stress varies over a test interval or other time interval. By way of further example and not by way of limitation, curve 16 may represent stress sensed at at least one test site on or in a mechanical component.

Curve 16 may be regarded as a collection of connected extrema. That is curve 16 may be regarded as connected succeeding peaks, or maxima and minima. Describing loci in graphic plot 10 using generally Cartesian-like coordinates, one may describe a point in graphic plot 10 as being located at coordinates described by the magnitude and time of the locus. Using such generally Cartesian-like coordinates, a coordinate of a locus in graphic plot 10 may be expressed as (amplitude, time). Accordingly, curve 16 connects minimum peak or locus $(m_1, t_1)$ with maximum peak or locus $(m_{12}, t_2)$, connects with minimum peak $(m_2, t_3)$, connects with maximum peak $(m_{11}, t_4)$, connects with minimum peak $(m_3, t_5)$, connects with maximum peak $(m_9, t_6)$, connects with minimum peak $(m_4, t_7)$, connects with maximum peak $(m_8, t_8)$, connects with minimum peak $(m_5, t_9)$, connects with maximum peak $(m_7, t_{10})$, connects with minimum peak $(m_6, t_{11})$ and connects with maximum peak $(m_{10}, t_{12})$.

One may observe that minima $(m_1, t_1)$, $(m_2, t_3)$, $(m_3, t_5)$, $(m_4, t_7)$ $(m_5, t_9)$, $(m_6, t_{11})$ are arranged in descending order of excursion toward axis 14. Similarly, one may observe that maxima $(m_{12}, t_2)$, $(m_{11}, t_4)$, $(m_9, t_6)$, $(m_8, t_8)$, $(m_7, t_{10})$ are arranged descending order of excursions away from axis 14. One may further observe that maximum $(m_{10}, t_{12})$ extends away from axis 14 beyond maxima $(m_9, t_6)$, $(m_8, t_8)$, $(m_7, t_{10})$ yet does not extend away from axis 14 beyond maxima $(m_{12}, t_2)$, $(m_{11}, t_4)$.

Rainflow counting methodology effects replacement of the earliest exceeded maxima with the exceeding maxima, and removes and separately accounts for exceeded excursion-sets as full cycles or half cycles as appropriate. In FIG. 1, rainflow counting therefore replaces maximum mg with maximum $m_{10}$. Counted cycles $20_1$, $20_2$, $20_3$ are bounded by extrema $(m_9, t_6)$, $(m_4, t_7)$, $(m_8, t_8)$, $(m_5, t_9)$, $(m_7, t_{10})$, $(m_6, t_{11})$ and associated vertical rainflow parallel with axis 14, indicated by dotted vertical rainflow indicating or "drip" lines $18_1$, $18_2$, $18_3$ in FIG. 1. Counted cycles $20_1$, $20_2$, $20_3$ are indicated using cross-hatching in FIG. 1. Preferably, counting data for counted cycles $20_1$, $20_2$, $20_3$ may be stored and accounted for in an aggregate accounting at the end of a testing interval or other juncture involving curve 16.

By orienting time axis 14 vertically, one may observe that a "flow of rain" down the contour of linked maxima and minima of curve 16 indicated by drip lines $18_1$, $18_2$, $18_3$ may be used to extract intermediate smaller magnitude counted cycles $20_1$, $20_2$, $20_3$ cycles and permit the relative maxima and minima to be matched in a hierarchy of largest to smallest magnitude cycles by extracting smaller cycles from larger cycles.

Figure 2:
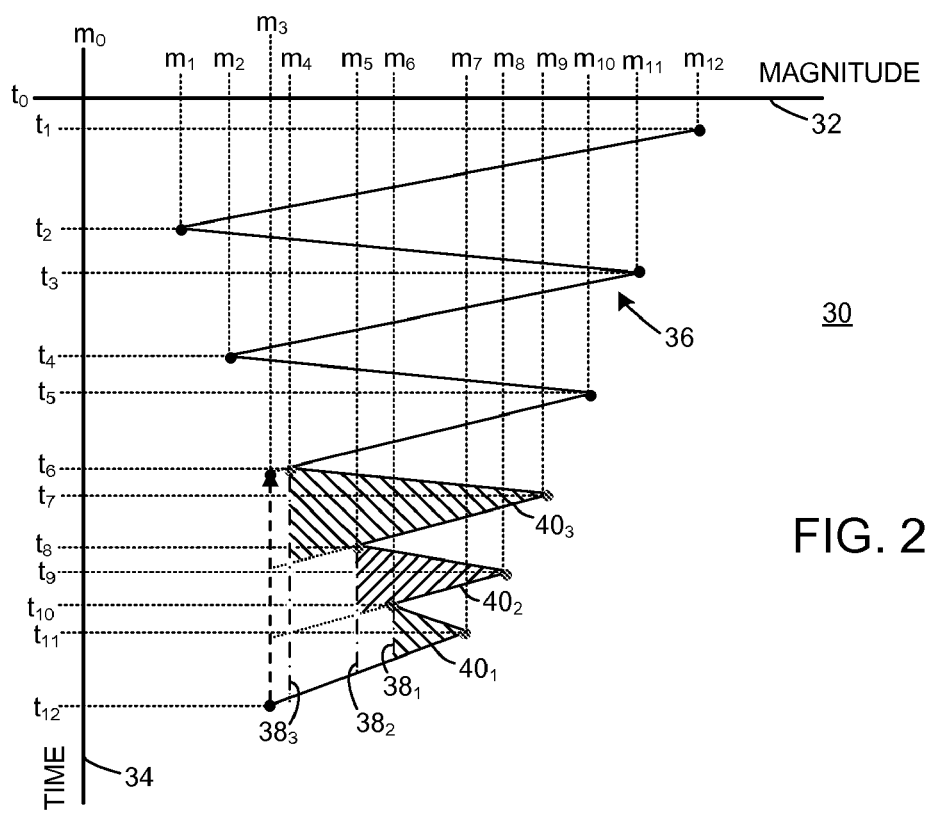
FIG. 2 is a graphic representation of evaluation of a minimum peak of a time varying signal vis-à-vis earlier-occurring minimum peaks of the signal.

FIG. 2 is a graphic representation of evaluation of a minimum peak of a time varying signal vis-à-vis earlier-occurring minimum peaks of the signal. In FIG. 2, a graphic plot 30 presents a horizontal axis 32 that may represent signal magnitude and a vertical axis 34 that may represent time. A curve 36 plotted against axes 32, 34 may represent a time-varying signal such as, by way of example and not by way of limitation, stress on a test member as stress varies over a test interval or other time interval. By way of further example and not by way of limitation, curve 36 may represent stress sensed at at least one test site on or in a mechanical component.

Curve 36 may be regarded as a collection of connected extrema. That is curve 36 may be regarded as connected succeeding peaks or maxima and minima. Describing loci in graphic plot 30 using generally Cartesian-like coordinates, one may describe a point in graphic plot 30 as being located at coordinates described by the amplitude and time of the locus. Thus, a coordinate of a locus in graphic plot 30 may be expressed as (amplitude, time). Accordingly, curve 36 connects maximum peak or locus $(m_{12}, t_1)$ with minimum peak or locus $(m_1, t_2)$, connects with maximum peak $(m_{11}, t_3)$, connects with minimum peak $(m_2, t_4)$, connects with maximum peak $(m_{10}, t_5)$, connects with minimum peak $(m_4, t_6)$, connects with maximum peak $(m_9, t_7)$, connects with minimum peak $(m_5, t_8)$, connects with maximum peak $(m_8, t_9)$, connects with minimum peak $(m_6, t_{10})$, connects with maximum peak $(m_7, t_{11})$ and connects with minimum peak $(m_3, t_{12})$.

One may observe that maxima $(m_{12}, t_1)$, $(m_{11}, t_3)$, $(m_{10}, t_5)$, $(m_9, t_7)$ $(m_8, t_9)$, $(m_7, t_{11})$ are arranged in descending order of excursion away from axis 34. Similarly, one may observe that minima $(m_1, t_2)$, $(m_2, t_4)$, $(m_4, t_6)$, $(m_5, t_8)$, $(m_6, t_{11})$ are arranged in descending order of excursions toward axis 34. One may further observe that minimum $(m_3, t_{12})$ extends toward axis 34 beyond minima $(m_4, t_6)$, $(m_5, t_8)$, $(m_6, t_{10})$ yet does not extend toward axis 34 beyond minima $(m_1, t_2)$, $(m_2, t_4)$.

Rainflow counting methodology effects replacement of the earliest exceeded minima with the exceeding minima, removes and separately accounts for exceeded excursion-sets as full cycles or half cycles as appropriate. In FIG. 2, rainflow counting therefore replaces minimum $m_4$ with minimum $m_3$. Counted cycles $40_1$, $40_2$, $40_3$ are bounded by extrema ($m_4$, $t_6$), ($m_9$, $t_7$), ($m_5$, $t_8$), ($m_8$, $t_9$), ($m_6$, $t_{10}$), ($m_7$, $t_{11}$) and associated vertical rainflow parallel with axis 34, indicated by dotted vertical rainflow indicating or "drip" lines $38_1$, $38_2$, $38_3$ in FIG. 2. Counted cycles $40_1$, $40_2$, $40_3$ are indicated using cross-hatching in FIG. 2. Preferably counting data for counted cycles $40_1$, $40_2$, $40_3$ may be stored and accounted for in an aggregate accounting at the end of a testing interval or other juncture involving curve 36.

By orienting time axis 34 vertically, one may observe that a "flow of rain" down the contour of linked maxima and minima of curve 36 indicated by drip lines $38_1$, $38_2$, $38_3$ may be used to extract intermediate smaller magnitude counted cycles $40_1$, $40_2$, $40_3$ cycles and permit the relative maxima and minima to be matched in a hierarchy of largest to smallest magnitude cycles by extracting smaller cycles from larger cycles.

Figure 3:
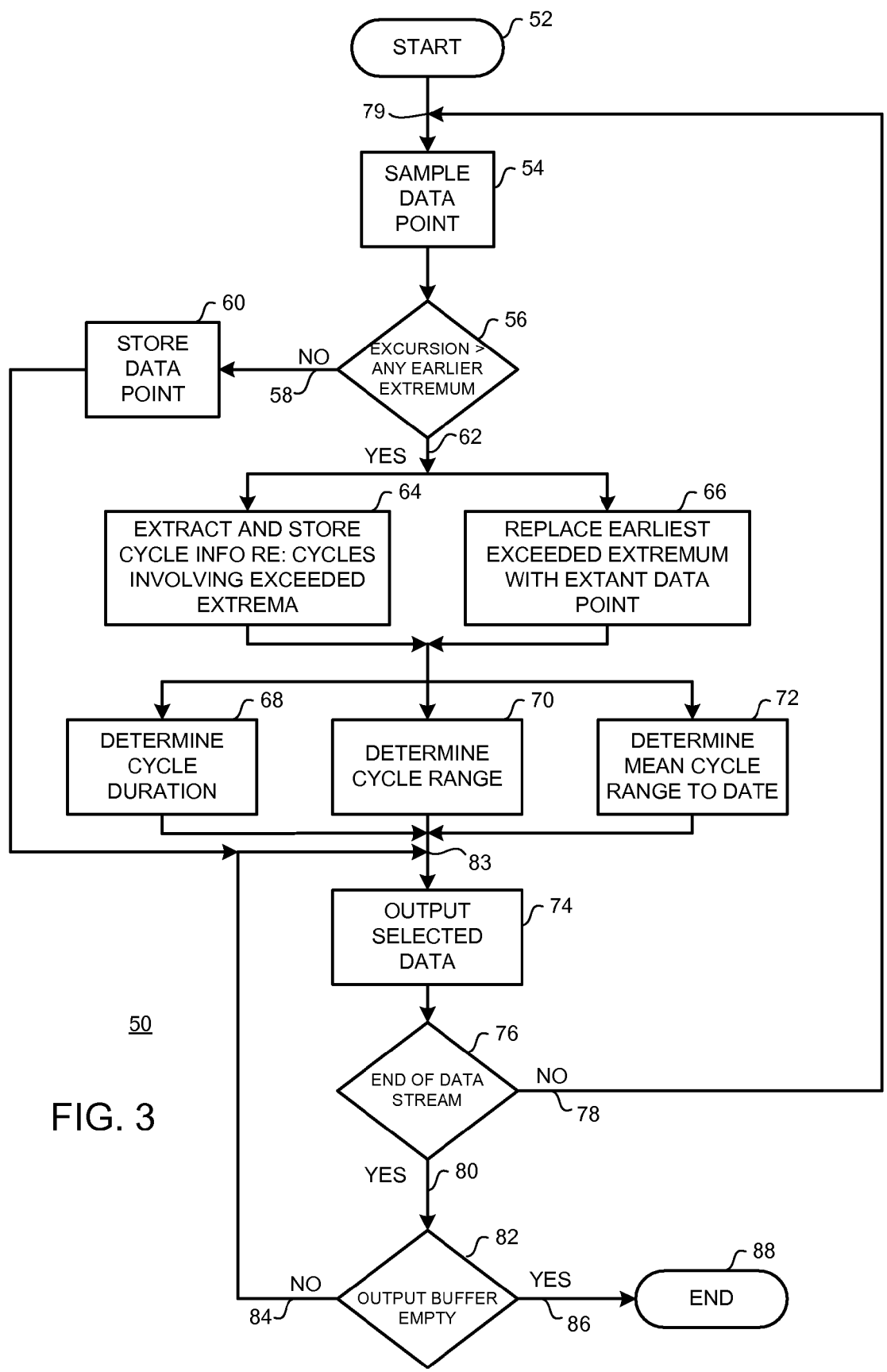
FIG. 3 is a flow chart illustrating an embodiment of a method of the disclosure.

FIG. 3 is a flow chart illustrating an embodiment of a method of the disclosure. In FIG. 3, a method 50 for evaluating a received signal representing values of a parameter varying over a test interval may begin at a START locus 52. Method 50 may continue by obtaining or sampling an extant data sample of the signal at an extant sample time, as indicated by a block 54. Method 50 may continue by posing a query whether the extant data sample exceeds at least one previous exceeded extremum of the signal, as indicated by a query block 56. If the extant data sample does not exceed the at least one previous exceeded extremum, method 50 may proceed from query block 56 via NO response line 58 and the extant data sample may be stored, as indicated by a block 60.

If the extant data sample exceeds the at least one previous exceeded extremum, method 50 may proceed from query block 56 via YES response line 62 and may, in no particular order: (1) extract and store cycle information involving the at least one previous exceeded extremum, as indicated by a block 64; and (2) replace an earliest exceeded extremum of the at least one previous exceeded extremum with the extant data sample, as indicated by a block 66.

Following performance of steps represented by blocks 64, 66 method 50 may continue by, in no particular order, (1) determining a cycle duration for an extant cycle involving the extant data sample, as indicated by a block 68; (2) determining a cycle range for the extant cycle involving the extant data sample, as indicated by a block 70; and (3) determining mean cycle range to date for selected cycles of the signal occurring up to the extant sample time, as indicated by a block 72.

Following performance of steps represented by blocks 68, 70, 72 method 50 may continue by outputting first selected data from a storage unit, as indicated by a block 74. The first selected data may include information determined by performance of steps represented by blocks 68, 70, 72.

Method 50 may continue by determining whether the test interval has completed, as indicated by a query block 76. If the test interval has not completed, method 50 may proceed from query block 76 via NO response line 78 to a locus 79, and steps represented by blocks 54, 56, 60, 64, 66, 68, 70, 72, 74, 76 may be repeated. If the test interval has completed, method 50 may proceed from query block 76 via YES response line 80 and may check whether an output buffer is empty, as indicated by a query block 82.

If the output buffer is not empty, method 50 may proceed from query block 82 via NO response line 84 to a locus 83, outputting second selected data from the output buffer, as indicated by block 74. Steps represented by blocks 76, 82 may thereafter be repeated. Second selected data outputted or presented according to block 74 may include full-cycle or half-cycle data (described in connection with FIGS. 1 and 2 above), information relating to data points stored according to block 60, or other data. If the output buffer is empty, method 50 may be terminated, as indicated by an END locus 88.

Figure 4:
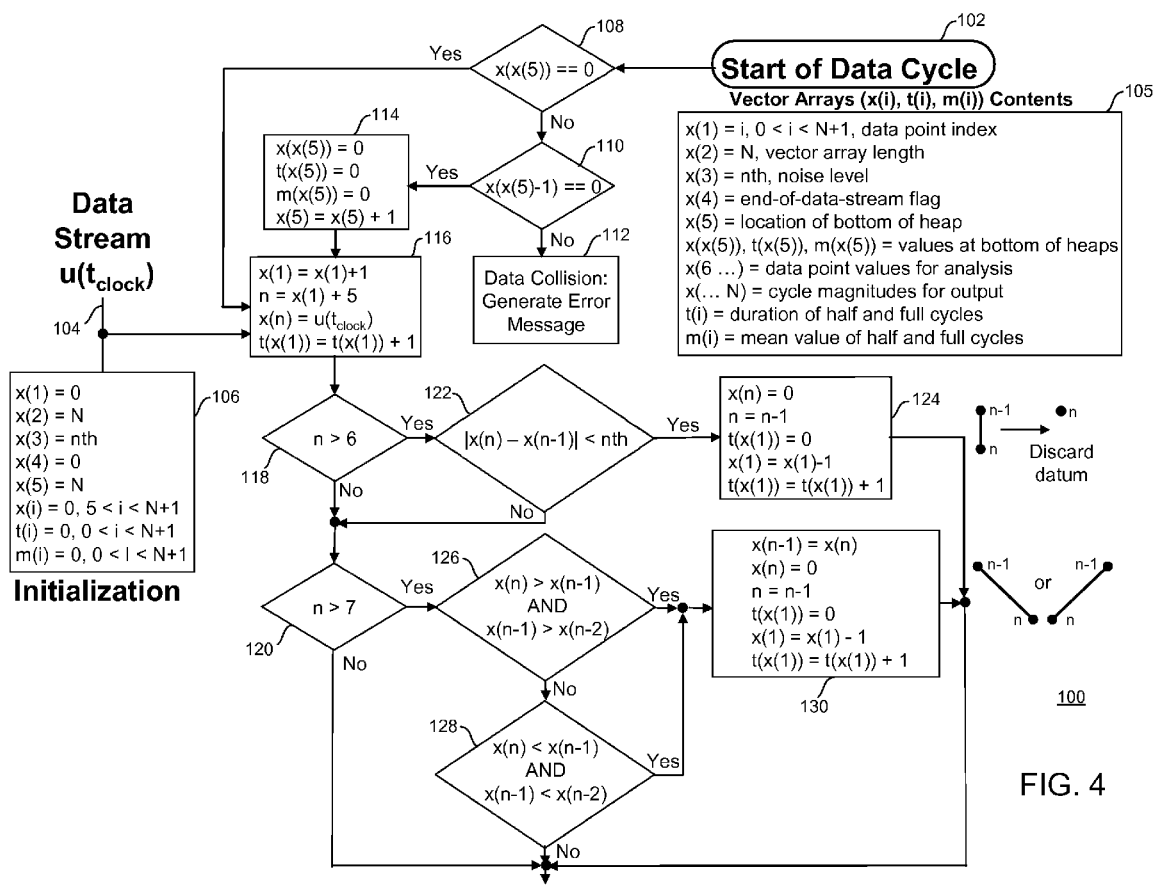
FIGS. 4-6 together present a flow chart illustrating details of an embodiment of a method of the disclosure.
Figure 5:
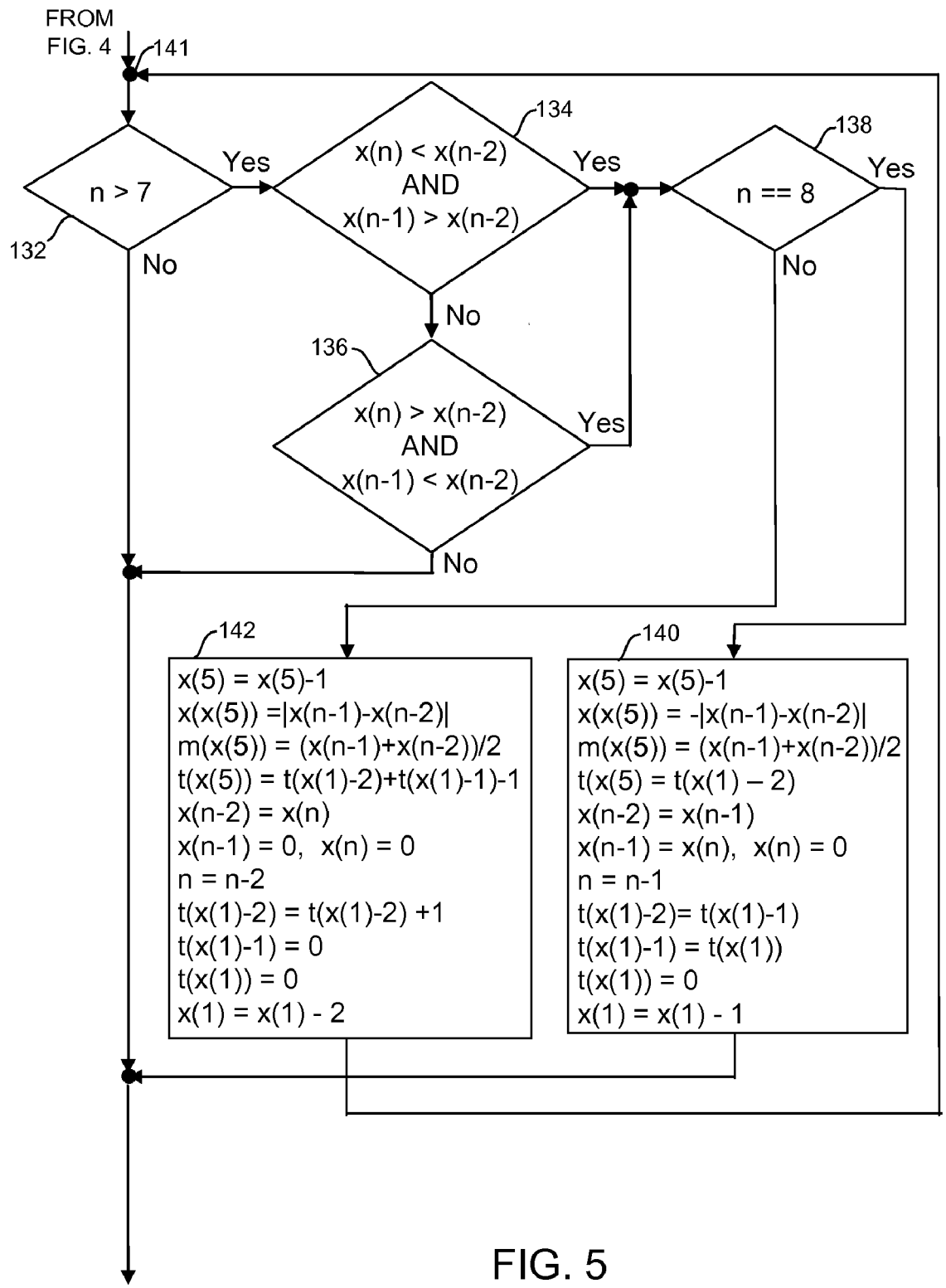
Figure 6:
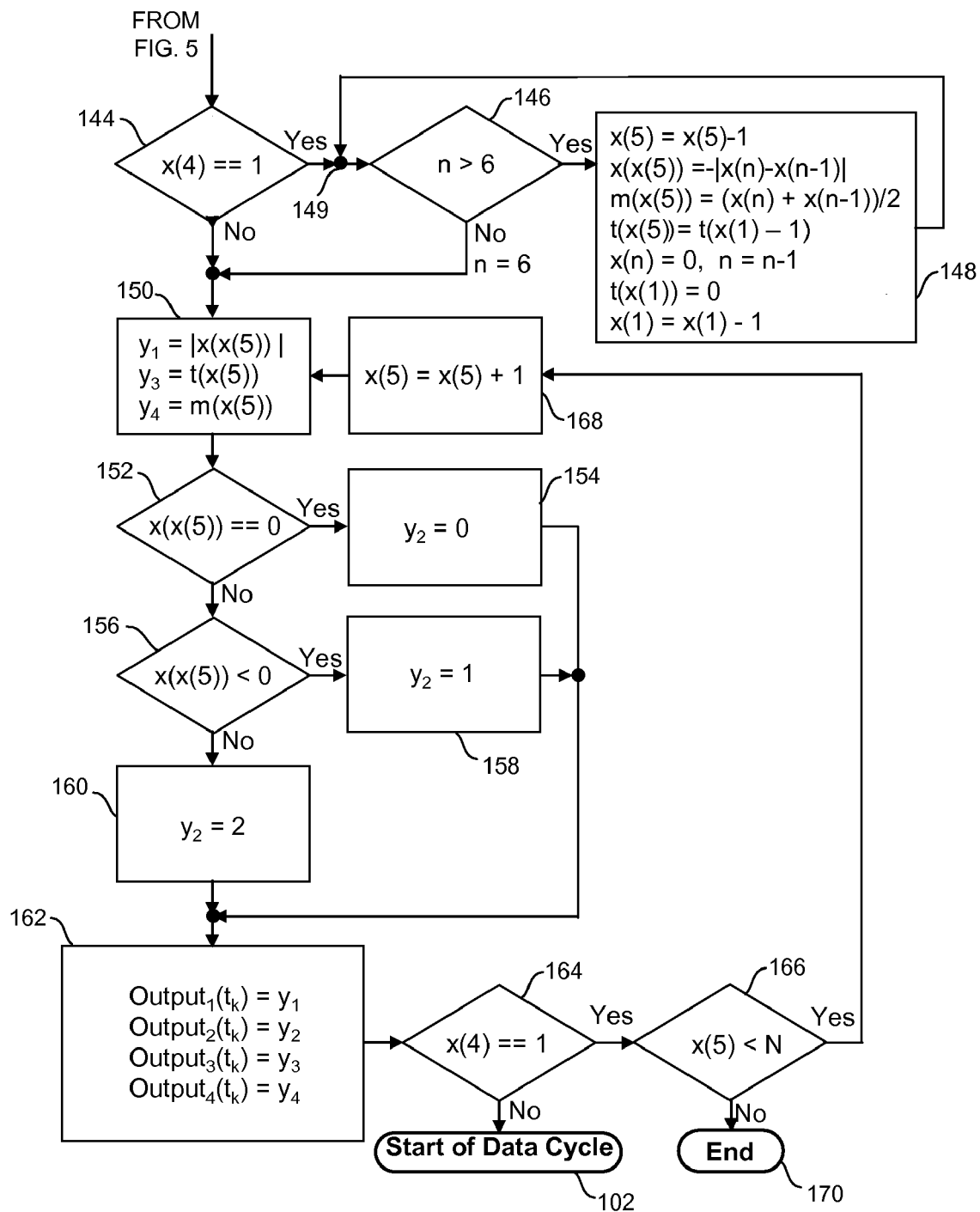

FIGS. 4-6 together present a flow chart illustrating details of an embodiment of a method of the disclosure. In FIG. 4, a method 100 begins at a START OF DATA CYCLE locus 102. A stream of data values may be clocked in at regular, known time intervals as a data stream signal $u(t_{clock})$ at an input locus 104. Processing may be performed using three vector arrays: $x(i)$, $t(i)$, $m(i)$. As summarized in an information block 105, vector array $x(i)$ may contain an index value at an array locus $x(1)$, an array length at an array locus $x(2)$, a noise threshold at an array locus $x(3)$, an end-of-data flag at an array locus $x(4)$, and a bottom-of-heap location at an array locus $x(5)$. The "heap" is a store of data stored for outputting or presenting according to predetermined steps of method 100. Accepted data values may be stored at the low end of vector array $x(i)$, from array locus $x(6)$ upward toward array locus $x(N)$, where N is the total storage available in vector array $x(i)$. Processed cycle magnitudes may be stored at the high end of vector array $x(i)$, from array locus $x(N)$ downward toward array locus $x(6)$. The heap may be the stored processed cycle magnitudes and other data stored from array locus $x(N)$ toward array locus $x(6)$.

If N is too small, a data "collision" may occur where accepted data values being stored from array locus $x(6)$ upward toward array locus $x(N)$ may "collide" with processed cycle magnitudes and other ready-for-presenting data stored from array locus $x(N)$ downward toward array locus $x(6)$. A "collision" may occur, for example when storage loci in vector array $x(i)$ are completely filled with stored data—loading from bottom upward from array locus $x(6)$ and loading from top downward from array locus $x(N)$—before all data can be stored. Such a data collision may be an error condition which may truncate or cease operation of method 100.

Vector arrays $t(i)$, $m(i)$ may store cycle duration and cycle mean amplitude values. Such a separation of processed data into three vector arrays $x(i)$, $t(i)$, $m(i)$ may permit processing of cycle duration and mean amplitude values to be optional.

Array element values may be initialized at the beginning of method 100 as indicated by a block 106. Array size N, stored in bottom-of-heap location array locus $x(5)$ may be determined by the total number of input data and cycle values one may expect to hold in vector array $x(i)$ at any one time. The number of input values may not exceed the maximum possible range divided by a noise threshold value. During each data, or clock, cycle, a datum may enter the low end of vector array $x(i)$ and a cycle range exits the top end of the array. If there are no cycle values to be outputted or presented, then the outputs, which may occur for each clock cycle, may be zero values, such as for cycle range $y_1$, cycle output type $y_2$, cycle time duration $y_3$, and cycle mean amplitude $y_4$ (see block 162; FIG. 6).

At the start of each data cycle, heap index at array locus $x(5)$ may be checked to determine if there are any actual contents in the heap, as indicated by a block 108. If heap index at array locus $x(5)$ is not equal to zero there may be heap contents and the vector element just below the bottom of the heap at array locus $x(x(5)-1)$ may be checked, as indicated by a block 110. If the vector element at array locus $x(x(5)-1)$ is not zero, there is a collision between the data array and the cycle array and a data collision error message may be issued, as indicated by a block 112. If a data array collision occurs, the value of N (the total storage available in vector array x(i)) may be increased. If x(x(5)) is not equal to zero, the cycle magnitude at array locus x(5) was outputted during the previous clock interval. As indicated by a block 114, values at array loci x(x(5)), t(x(4)), and m(x(5)) may be set to zero; value at array locus x(5)may be incremented so that it indicates that bottom of the heap is located one element closer to the top of the heap, array locus x(N).

At a block 116 the data point index value at array locus x(1) may be incremented and then may be added to 5 to determine a data point location index n. The data stream input value u($t_{clock}$), occurring during a clock interval k, may be placed into array locus x(n) and the time value at t(x(1)) may be incremented. So long as a constant clock interval duration time is provided, one may accumulate the numbers of clock intervals corresponding to keep track of half cycle and full cycle values of data stream input signal u($t_{clock}$).

At a block 118 the value of data point location index n may be analyzed to determine if there is more than one (n=6) data point in vector array x(i). The value (n=6) is selected because the lower five values are occupied by contents of vector array x(i) (see block 105). If there are not more than one data point in vector array x(i), method 100 passes through blocks 120 and 132 (FIG. 5) and proceeds to block 144 (FIG. 6). If there are more than one data point in vector array x(i), then at a block 122 the difference between adjacent vector array values x(n) and x(n−1) is checked to determine if that difference is less than a predetermined noise threshold nth. If the difference between adjacent vector array values x(n) and x(n−1)is not less than noise threshold nth, method 100 proceeds to block 120. If the difference between adjacent vector array values x(n) and x(n−1)is less than noise threshold nth, the difference between array values x(n) and x(n−1) may be regarded as being insignificant. The data point stored in vector array locus x(n) may be set to zero; data point location index n may be decremented; the corresponding clock time value, which was 1 for the new datum, may be set to zero; value stored at array locus x(1) may be decremented. These actions—indicated by a block 124 may absorb the new data point into the previous one. This result is why the associated time value t(x(1)) may be incremented. The process step represented by block 124 is illustrated adjacent block 124 in FIG. 4: the two most recent data values n, n−1 are depicted as points having horizontal positions corresponding to their data values and having vertical positions relating to time of occurrence of the data values. Time increases in the downward direction. Because the value of datum n is close to that of datum n−1, the datum at array locus x(n) may be discarded and data point location index n may be decremented, so that what had been n−1 becomes n.

At block 120 the value of point location index n may be analyzed to determine if there are more than two (n=7) data points in the data array. If there are not more than two data points in the data array, method 100 may proceed through block 132 (FIG. 5) to block 144 (FIG. 6). If there are more than two (n>7) data points in the data array, then at block 126 the value at array locus x(n) may be compared with the value at array locus x(n−1), and the value at array locus x(n−1) may be compared with the value at array locus x(n−2). If there is a series of increasing values from array locus n−2 to array locus n, then the progression of values from array locus n−2 to array locus n is monotonic. When such a monotonic relationship is present, the middle datum x(n−1) may be discarded, as indicated in a block 130. The process step represented by block 130 is illustrated adjacent block 130: the value in array locus x(x(n−1)) may set at the value of element in array locus x(x(n)), data point location index n may be decremented, the time duration of the original datum t(x(1)) may be set to zero, data point index x(1) may be decremented, and the time duration of the new element x(n) may be incremented so that t(x(1))=t(x(1))+1. Method 100 may then proceed from block 130 to block 132 (FIG. 5). If there is no series of increasing values from array locus n−2 to array locus n, at block 126, method 100 proceeds 128 to check the same series that had been checked as indicated by block 126 to determine if the vector element values decrease from n−2 through n. If the vector element values decrease from n−2 through n method 100 proceeds through block 130 and then to block 132. If the vector element values do not decrease from n−2 through n, method 100 proceeds directly to block 132. Depending upon the programming language used to implement this invention, as well as upon the preference of the programmer, it may be possible combine block 124 with block 130 and provide in programming for executing the step x(n−1)=x(n) (performed in block 130; FIG. 4) as an option.

Referring to FIG. 5, at block 132 the value of n, which may have changed since its initialization at block 116, may again be checked to determine if n is greater than 7. If n is not greater than 7, method 100 may proceed to block 144 (FIG. 6). If n is greater than 7, checks may be made at blocks 134, 136 to determine if there is "rainflow" from x(n−2) to the link between n and n−1 (see FIGS. 1 and 2). If queries posed by either of blocks 134, 136 are answered "YES", then method 100 may proceed to block 138 by which a query may be posed to determine if there are only three data points in the data array, or "rainflow stack". If there are only three data points in the data array there is a half cycle at the top of the stack and method 100 may proceed to block 140. At block 140, the heap counter x(5) may be decremented; the negative value of the difference between x(n−1) and x(n−2) (signifying half cycle) may be placed in x(x(5)) at the bottom of the x-heap (the x-heap may contain x values for presentation); the mean value (x(n−1)+x(n−2))/2 may be placed at the bottom of the m-heap (the m-heap may contain mean values for presentation); the time duration between x(n−2) and x(n−1) may be placed at the bottom of the t-heap (the t-heap may contain time duration data for presentation); x(n−2) may be changed to x(n−1), the new top of the rainflow stack; x(n−1) may become x(n) and x(n) may become zero; the value of data point location index n may be decremented; the time duration between the new x(n−1) and x(n) may be corrected to its original value; t(x(1)−2))=t(x(1)−1); the time duration for the new x(n) is similarly reset; t(x(1) may be zeroed and x(1) may be decremented. After block 140 operations are completed, method 100 may proceed to block 144.

If at block 138 it is determined that there are more than three data points in the rainflow stack (n>8), method 100 may proceed to block 142 for extraction of a full cycle to the heap. At block 142, the heap counter x(5) (see block 105; FIG. 4) may be decremented; the positive difference (signifying full cycle) value of the difference between x(n−1) and x(n−2) may be placed in x(x(5)) at the bottom of the x-heap; the mean value (x(n−1)+x(n−2))/2 may be placed at the bottom of the m-heap; time duration from x(n−2) to x(n) may be placed at the bottom of the t-heap. The value of 1, one time increment, may be subtracted from this sum to account for the portion of the separation between x(n) and x(n−1) not included in the extracted cycle. The value of x(n−2) may be readjusted to x(n); x(n−1) and x(n) may be set to zero; n may be decremented twice to n−2. The time duration separating the new x(n) and x(n−1) may be set to the old (t(x(1)−2) plus 1, to account for the portion of the old x(n)−x(n−1) not absorbed by the cycle extracted to the heap. The values of $t(x(1))-1$ and $t(x(1))$ may be set to zero and data point index $x(1)$ may be decremented twice. After processing represented by block 142 method 100 may return to block 132 to check the value of the new n to look for any more half or full rainflow cycles that may have been generated by the acquisition of the original $x(n)$. If there are no more cycles, method 100 may proceed to block 144 (FIG. 6).

Referring to FIG. 6, at block 144, the value of the end-of-data-stream flag value $x(4)$ may be checked. If end-of-data-stream flag value $x(4)$ equals 0, the flag has not been set, there may be more incoming data to be analyzed, and method 100 may proceed to block 150. If end-of-data-stream flag value $x(4)$ equals 1, the flag has been set by an external signal, and method 100 may proceed to block 146. At block 146, method 100 may check the value of n to determine if there are any data points in data point array $x(i)$. If n equals 6 there may be one final datum in the rainflow stack and all cycles may have been dumped to the heap. Method 100 may then proceed to block 150. If n exceeds 6, there may be two or more data points in the stack and method 100 may proceed to block 148. At block 148, method 100 may insert the differences between successive data points as half cycles to the x-heap, along with associated mean values to the m-heap and time durations to the t-heap. Blocks 146, 148 may operate in succession until all data cycles left in the data stack has been transferred to a heap for extraction by blocks 150 through 168.

At block 150, the parameter $y_1$ may be assigned a value indicating cycle magnitude in $x(x(5))$, the x-value at the bottom of the x-heap. Parameter $y_3$ may be assigned a value indicating cycle duration in $t(x(5))$, the t-value at the bottom of the t-heap. Parameter $y_4$ may be assigned a value indicating cycle mean value in $m(x(5))$, the m-value at the bottom of the m-heap. Method 100 may proceed to block 152 where the cycle value $x(x(5))$ may be checked to determine if it is zero. Cycle value $x(x(5))$ being zero may signify that no value is to be outputted for this extant clock interval. If $x(x(5))$ is equal to zero, the value of $y_2$ may be set to zero at block 154 and method 100 may proceed to block 162. If $x(x(5))$ is not equal to zero, method 100 may proceed to block 156 to determine if the cycle value $x(x(5))<0$, signifying a half cycle. If the cycle value $x(x(5))<0$, the value of $y_2$ may be set to 1 in block 158 and method 100 may proceed to block 162. If the cycle value $x(x(5))$ is not less than 0, then cycle value $x(x(5))$ must be $>0$ because it was determined in block 152 that $x(x(5))$ is not=0. Cycle value $x(x(5))$ being greater than 0 signifies a full cycle, the magnitude of the cycle being indicated by the contents in vector array locus magnitude in $x(x(5))$, $y_2$ may be set to 2 and method 100 may proceed to block 162.

At block 162, method 100 may output or present the values of $y_1$, $y_2$, $y_3$, $y_4$ for the current or extant clock interval. If there is no data in the heaps, all four values may be zero. If there is a half cycle from $x(x(5))$, $y_2$ may equal 1. If there is a full cycle from $x(x(5))$, $y_2$ may equal 2. From block 162, method 100 may proceed to block 164 where end-of-data-stream flag $x(4)$ may be checked. If end-of-data-stream flag $x(4)$ is zero, method 100 may return to START OF DATA CYCLE locus 102 (FIG. 4) to effect execution of a next clock interval with receipt of a next data point at input locus 104. If end-of-data-stream flag $x(4)$ equals 1, method 100 may proceed to block 166 to check the value of bottom of heap indicator $x(5)$. If bottom of heap indicator $x(5)<N$, there may be more data in the heaps to be outputted or presented and method 100 may proceed to block 168 for the incrementing of bottom of heap indicator $x(5)$ toward N. Method 100 may then proceed to block 150 and steps represented by blocks 152 through 168 may be repeated until bottom of heap indicator $x(5)$ is not less than N. When bottom of heap indicator $x(5)$ is not less than N, method 100 may terminate at END locus 170.

Regarding FIG. 1 together with FIGS. 4-6, one may observe how method 100 may effect some of its operations. FIG. 1 depicts how a data stack $x(n)$ may appear after a substantial number of clock intervals, so that the intervals illustrated in FIG. 1 may represent data stack $x(n)$ where n=6, 7, 8, . . . . One skilled in the art of signal evaluation may understand application of method 100 to the exemplary signal illustrated in FIG. 2 as well In the interest of avoiding prolixity, only FIG. 1 will be discussed in detail with respect to method 100.

In FIG. 1, data point n=6 may correspond with minimum locus $(m_1, t_1)$, data point n=7 may correspond with maximum locus $(m_{12}, t_2)$, data point n=8 may correspond with minimum locus $(m_2, t_3)$, data point n=9 may correspond with maximum locus $(m_{11}, t_4)$, data point n=10 may correspond with minimum locus $(m_3, t_5)$, data point n=11 may correspond with maximum locus $(m_9, t_6)$, data point n=12 may correspond with minimum locus $(m_4, t_7)$, data point n=13 may correspond with maximum locus $(m_8, t_8)$, data point n=14 may correspond with minimum locus $(m_5, t_9)$, data point n=15 may correspond with maximum locus $(m_7, t_{10})$, data point n=16 may correspond with minimum locus $(m_6, t_{11})$, data point n=17 may correspond with maximum locus $(m_{10}, t_{12})$.

Data points $x(6)$ through $x(16)$ in FIG. 1 may represent data that have been earlier processed through rainflow treatment and have had smaller intermediate value cycles, upon which "rain" had flowed, extracted to the heap. For data appearing through data point $x(16)$ there is a decreasing hierarchy of maxima and minima established. However, data point $x(17)$ exceeds previous maxima $x(15)$, $x(13)$, $x(11)$. "Rain" may flow from maximum locus $x(11)$, from maximum locus $x(13)$ and from maximum locus $x(15)$ onto the link or signal segment between loci $x(17)$, $x(16)$. Executing block 142 of method 100 (FIG. 5) may effect extracting the lowest cycle of magnitude $|x(16)-x(15)|$ to the heap. Method 100 may proceed from block 142 to locus 141 and thence to block 132 and eventually to block 142 to effect detecting and extracting the next cycle of magnitude $|x(14)-x(13)|$. Method 100 may proceed from block 142 to locus 141 and thence to block 132 and eventually to block 142 to effect detecting and extracting the next cycle of magnitude $|x(12)-x(11)|$. At this portion of the data analysis, there may be no more cycles to be extracted and what had been data point $x(11)$ may be assigned the value of data point $x(17)$, so that the value of data point $x(17)$ becomes the new value of data point $x(11)$. Data point $x(11)$ is now the bottom extent of the data stack.

If, by way of further example, another data point $x(16A)$ is present in the data signal represented by curve 10 (FIG. 1), and data point $x(17)$ exceeds the previous minima and maxima, but in the same direction as data point $x(16A)$, this situation may be detected by block 126 (block 128 may detect a similar situation in data signal 30; FIG. 2). Block 130 may eliminate data point $x(16A)$ and may designate a new data point $x(16A)$ as having the value of the old data point $x(17)$.

If there are only three data points, such as data points $x(6)$, $x(7)$, $x(8)$ and signal excursions are detected such that $|x(8)-x(7)|>|x(7)-x(6)|$, then one of blocks 134, 136 may detect this situation and may extracts $|x(8)-x(7)|$ from the data stack as a half cycle.

An alternative treatment of such a three data point situation may provide for exchanging the values in data loci $x(6)$ and $x(8)$, along with their respective time duration values. Instead of extracting the half cycle, this alternate treatment may transform the half cycle to the stack's second half cycle and may store the extracted half-cycle for later joining with another data point to effect extraction of a full cycle. Additional method steps may be employed for carrying out the required joining of half-cycles to effect extraction of a full cycle. Such additional method steps are within the understanding of one skilled in the art of signal evaluation and will not be repeated here in the interest of avoiding prolixity.

In carrying out such an alternate signal treatment, one may replace logic set forth in block 140 (FIG. 5) with the following logical treatment:

$$A = x(n-2)$$

$$x(n-2) = x(n)$$

$$x(n) = A$$

$$A = t(x(1)-2)$$

$$t(x(1)-2) = t(x(1)-1)$$

$$t(x(1)-1) = A$$

$$t(x(1)) = 1$$

where A is a dummy intermediate parameter.

Figure 7:
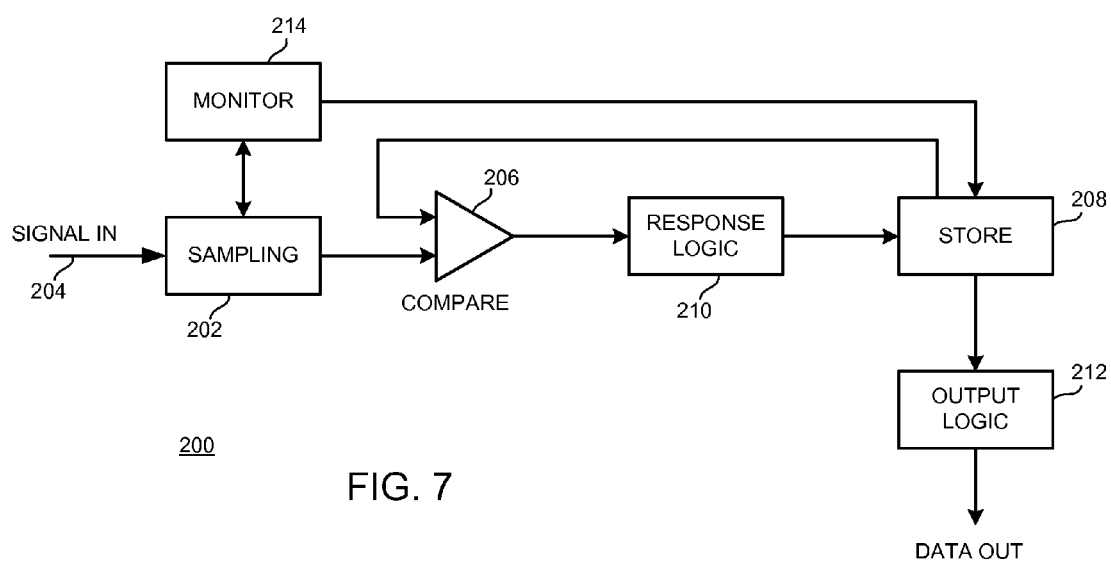
FIG. 7 is a schematic illustrating an embodiment of an apparatus of the disclosure.

FIG. 7 is a schematic illustrating an embodiment of an apparatus of the disclosure. In FIG. 7, an apparatus 200 for evaluating a received signal representing values of a parameter varying over a test interval includes a signal sampling unit 202. Signal sampling unit 202 may be coupled with an input locus 204 for sampling the received signal. Signal sampling unit 202 obtains an extant data sample of the signal at an extant sample time. A comparing unit 206 may be coupled with sampling unit 202 and may be coupled with a storage unit 208. Comparing unit 206 may determine whether the extant data sample exceeds at least one previous exceeded extremum of the signal stored in storage unit 208.

A responsive unit 210 may be coupled with comparing unit 206. If the comparing performed by comparing unit 206 indicates the extant data sample does not exceed at least one previous exceeded extremum, responsive unit 210 may effect storing of the extant data sample in storage unit 208. If the extant data sample exceeds at least one previous exceeded extremum, responsive unit 210 may, in no particular order, (1) effect a first response extracting and storing cycle information involving the previous exceeded extremum or extrema in storage unit 208; and (2) effect a second response replacing an earliest exceeded extremum of the previous exceeded extremum or extrema in storage unit 208 with the extant data sample.

An output unit 212 may be coupled with storage unit 208. Output unit 212 may effect outputting or presenting first selected data from storage unit 208 at least one time during the test interval.

A signal monitoring unit 214 may be coupled with signal sampling unit 202 and with storage unit 208. Signal monitoring unit 214 may determine when the test interval has completed. Signal monitoring unit 214 and the signal sampling unit 202 may cooperate to obtain a next extant data sample of the signal at input locus 204 at a next extant sample time when the test interval is not complete.

Apparatus 200 may effect treatment of the next extant data sample substantially as the treatment of the first extant data was effected. When the test interval is completed and storage unit 208 is not empty, signal monitoring unit 214 and signal sampling unit 202 may cooperate to cease sampling the signal and present second selected data from storage unit 208. When the test interval is completed and storage unit 208 is empty, signal monitoring unit 214 and signal sampling unit 202 may cooperate to cease sampling the signal.

It is to be understood that, while the detailed drawings and specific examples given describe preferred embodiments of the invention, they are for the purpose of illustration only, that the apparatus and method of the invention are not limited to the precise details and conditions disclosed and that various changes may be made therein without departing from the spirit of the invention which is defined by the following claims:

I claim:

1. A method for evaluating a received signal representing values of a parameter varying over a test interval; said received signal being embodied in a plurality of connected extrema; the method comprising:
    (a) employing a sampling unit configured for receiving said received signal for obtaining an extant data sample of said signal at an extant sample time;
    (b) employing a comparing unit for comparing said extant data sample with stored previous extrema of said plurality of connected extrema stored in a storage unit to effect determining whether said extant data sample exceeds at least one of said stored previous extrema;
    (c) employing a logic unit for determining whether said extant data sample exceeds at least one of said stored previous extrema; if said extant data sample does not exceed at least one of said stored previous extrema, storing said extant data sample;
    (d) if said extant data sample exceeds at least one of said stored previous extrema to establish at least one currently-exceeded previous extremum, in no particular order:
        (1) extracting and storing cycle information in said storage unit involving each respective said currently-exceeded previous extremum of said at least one currently-exceeded previous extremum; and
        (2) replacing an earliest-occurring currently-exceeded previous extremum of said at least one currently-exceeded previous extremum stored in said storage unit with said extant data sample;
    (e) outputting first selected data from said storage unit;
    (f) employing a monitoring unit coupled with said sampling unit for determining whether said test interval has completed;
    (g) if said test interval has not completed, repeating steps (a) through (f);
    (h) if said test interval has completed, checking whether said storage unit is empty;
    (i) if said storage unit is not empty, outputting second selected data from said storage unit; and
    (j) if said storage unit is empty, terminating the method.

2. A method for evaluating a received signal representing values of a parameter varying over a test interval as recited in claim 1 wherein the method further comprises at least one of the following steps performed in no particular order following performance of steps (d)(1) and (d)(2):
    (d)(3) determining a cycle duration for an extant cycle involving said extant data sample;
    (d)(4) determining a cycle range for said extant cycle involving said extant data sample; and
    (d)(5) determining mean cycle range to date for selected cycles of said signal occurring up to said extant sample time.

3. A method for evaluating a received signal representing values of a parameter varying over a test interval as recited in claim 2 wherein said first selected data includes at least one of said extant data sample and said cycle information involving each respective said currently-exceeded previous extremum; and wherein said second selected data includes at least one of said cycle duration for an extant cycle involving said extant data sample, said cycle range for said extant cycle involving said extant data sample, and said mean cycle range to date for selected cycles of said signal occurring up to said extant sample time.

4. A method for evaluating a received signal representing values of a parameter varying over a test interval as recited in claim 3 wherein said outputting second selected data from said storage unit is effected by steps comprising:
  (i)(1) determining whether an early-occurring stored data entry in said storage unit exceeds at least one later-occurring stored extremum of said stored data samples;
  (i)(2) if said early-occurring stored data entry does not exceed said at least one later-occurring stored extremum, storing said early-occurring stored data entry in said storage unit;
  (i)(3) if said early-occurring stored data entry exceeds said at least one later-occurring stored extremum, in no particular order:
    (i)(3)[a] extracting and outputting cycle information involving said at least one later-occurring stored extremum; and
    (i)(3)[b] replacing a latest-exceeded extremum of said at least one later-occurring stored extremum with said early-occurring stored data entry;
  (i)(4) continuing performing steps (i)(1) through (i)(3) for a next-early-occurring stored data entry until no later-occurring stored extremum is exceeded; and
  (i)(5) in no particular order:
    (i)(5)[a] outputting stored said early-occurring stored data entries from said storage unit; and
    (i)(5)[b] outputting remaining later-occurring stored data entries in said storage unit.

5. A method for evaluating a received signal representing values of a parameter varying over a test interval as recited in claim 2 wherein said outputting second selected data from said storage unit is effected by steps comprising:
  (i)(1) determining whether an early-occurring stored data entry in said storage unit exceeds at least one later-occurring stored extremum of said stored data samples;
  (i)(2) if said early-occurring stored data entry does not exceed said at least one later-occurring stored extremum, storing said early-occurring stored data entry in said storage unit;
  (i)(3) if said early-occurring stored data entry exceeds said at least one later-occurring stored extremum, in no particular order:
    (i)(3)[a] extracting and outputting cycle information involving said at least one later-occurring stored extremum; and
    (i)(3)[b] replacing a latest-exceeded extremum of said at least one later-occurring stored extremum with said early-occurring stored data entry;
  (i)(4) continuing performing steps (i)(1) through (i)(3) for a next-early-occurring stored data entry until no later-occurring stored extremum is exceeded; and
  (i)(5) in no particular order:
    (i)(5)[a] outputting stored said early-occurring stored data entries from said storage unit; and
    (i)(5)[b] outputting remaining later-occurring stored data entries in said storage unit.

6. A method for evaluating a received signal representing values of a parameter varying over a test interval as recited in claim 1 wherein said first selected data includes at least one of said extant data sample and said cycle information involving each respective said currently-exceeded previous extremum.

7. A method for evaluating a received signal representing values of a parameter varying over a test interval as recited in claim 6 wherein said outputting second selected data from said storage unit is effected by steps comprising:
  (i)(1) determining whether an early-occurring stored data entry in said storage unit exceeds at least one later-occurring stored extremum of said stored data samples;
  (i)(2) if said early-occurring stored data entry does not exceed said at least one later-occurring stored extremum, storing said early-occurring stored data entry in said storage unit;
  (i)(3) if said early-occurring stored data entry exceeds said at least one later-occurring stored extremum, in no particular order:
    (i)(3)[a] extracting and outputting cycle information involving said at least one later-occurring stored extremum; and
    (i)(3)[b] replacing a latest-exceeded extremum of said at least one later-occurring stored extremum with said early-occurring stored data entry;
  (i)(4) continuing performing steps (i)(1) through (i)(3) for a next-early-occurring stored data entry until no later-occurring stored extremum is exceeded; and
  (i)(5) in no particular order:
    (i)(5)[a] outputting stored said early-occurring stored data entries from said storage unit; and
    (i)(5)[b] outputting remaining later-occurring stored data entries in said storage unit.

8. A method for evaluating a received signal representing values of a parameter varying over a test interval as recited in claim 1 wherein said outputting second selected data from said storage unit is effected by steps comprising:
  (i)(1) determining whether an early-occurring stored data entry in said storage unit exceeds at least one later-occurring stored extremum of said stored data samples;
  (i)(2) if said early-occurring stored data entry does not exceed said at least one later-occurring stored extremum, storing said early-occurring stored data entry in said storage unit;
  (i)(3) if said early-occurring stored data entry exceeds said at least one later-occurring stored extremum, in no particular order:
    (i)(3)[a] extracting and outputting cycle information involving said at least one later-occurring stored extremum; and
    (i)(3)[b] replacing a latest-exceeded extremum of said at least one later-occurring stored extremum with said early-occurring stored data entry;
  (i)(4) continuing performing steps (i)(1) through (i)(3) for a next-early-occurring stored data entry until no later-occurring stored extremum is exceeded; and
  (i)(5) in no particular order:
    (i)(5)[a] outputting stored said early-occurring stored data entries from said storage unit; and
    (i)(5)[b] outputting remaining later-occurring stored data entries in said storage unit.

9. An apparatus for evaluating a received signal representing values of a parameter varying over a test interval; the apparatus comprising:
  (a) a signal sampling unit coupled for sampling said received signal; said signal sampling unit obtaining an extant data sample of said signal at an extant sample time;
  (b) a comparing unit coupled with said sampling unit and coupled with a storage unit; said comparing unit determining whether said extant data sample exceeds at least one previous extremum of said signal stored in said storage unit;

(c) a responsive unit coupled with said comparing unit; if said comparing indicates said extant data sample does not exceed said at least one previous extremum, said responsive unit effects storing of said extant data sample in said storage unit; if said extant data sample exceeds said at least one previous extremum to establish at least one currently-exceeded previous extremum, said responsive unit, in no particular order, effects a first response extracting and storing cycle information in said storage unit involving each respective currently-exceeded previous extremum of said at least one currently-exceeded previous extremum; and effects a second response replacing an earliest-occurring currently-exceeded previous extremum of said at least one currently-exceeded previous extremum in said storage unit with said extant data sample;

(d) an output unit coupled with said storage unit; said output unit effecting outputting first selected data from said storage unit at least one time during said test interval; and (e) a signal monitoring unit coupled with said signal sampling unit and with said storage unit; said signal monitoring unit determining when said test interval has completed;

said signal monitoring unit and said signal sampling unit cooperating to obtain a next extant data sample of said signal at a next extant sample time when said test interval is not complete; the apparatus effecting treatment of said next extant data sample substantially as said treatment of said first extant data was effected; when said test interval is completed and said storage unit is not empty, said signal monitoring unit and said signal sampling unit cooperate to cease sampling said signal and present second selected data from said storage unit; when said test interval is completed and said storage unit is empty, said signal monitoring unit and said signal sampling unit cooperate to cease sampling said signal.

10. An apparatus for evaluating a received signal representing values of a parameter varying over a test interval as recited in claim 9 wherein, following said first and second responses, said responsive unit, in no particular order, effects a third response determining a cycle duration for an extant cycle involving said extant data sample; effects a fourth response determining a cycle range for said extant cycle involving said extant data sample; and effects a fifth response determining mean cycle range to date for selected cycles of said signal occurring up to said extant sample time.

11. An apparatus for evaluating a received signal representing values of a parameter varying over a test interval as recited in claim 10 wherein said first selected data includes at least one of said extant data sample and said cycle information involving said at least one currently-exceeded previous extremum; and wherein said second selected data includes at least one of said cycle duration for an extant cycle involving said extant data sample, said cycle range for said extant cycle involving said extant data sample, and said mean cycle range to date for selected cycles of said signal occurring up to said extant sample time.

12. An apparatus for evaluating a received signal representing values of a parameter varying over a test interval as recited in claim 9 wherein said first selected data includes at least one of said extant data sample and said cycle information involving said at least one currently-exceeded previous extremum.

* * * * *